(12) United States Patent
Greer et al.

(10) Patent No.: US 7,439,415 B2
(45) Date of Patent: Oct. 21, 2008

(54) POPULATION OF HOXB8 MUTANTS AND USES IN IDENTIFYING AGENTS FOR TREATING REPETITIVE BEHAVIORS

(76) Inventors: Joy M. Greer, 618 N. DeSota St., Salt Lake City, UT (US) 84103; Mario R. Capecchi, 2529 E. 1300S, Salt Lake City, UT (US) 84108

( * ) Notice: Subject to any disclaimer, the term of this patent is extended or adjusted under 35 U.S.C. 154(b) by 382 days.

(21) Appl. No.: 10/479,148

(22) PCT Filed: May 31, 2002

(86) PCT No.: PCT/US02/17611

§ 371 (c)(1),
(2), (4) Date: May 21, 2004

(87) PCT Pub. No.: WO02/096470

PCT Pub. Date: Dec. 5, 2002

(65) Prior Publication Data

US 2004/0197353 A1    Oct. 7, 2004

Related U.S. Application Data

(60) Provisional application No. 60/295,494, filed on May 31, 2001.

(51) Int. Cl.
*A01K 67/00* (2006.01)
*A61K 49/00* (2006.01)
(52) U.S. Cl. .......................................... 800/9; 424/9.2
(58) Field of Classification Search ....................... None
See application file for complete search history.

(56) References Cited

OTHER PUBLICATIONS

Pato et al. The Genetics of Obsessive-Compulsive Disorder; Current Psychiatry Reports, vol. 3, No. 2 (2001) pp. 163-168.*
Stein et al. Neurobiology of the Obsessive-Compulsive Spectrum Disorders; Biol. Psychiatry, vol. 47 (2000) pp. 296-304.*
Araki et al., "Site-specific recombination of a transgene in fertilized eggs by transient expression of Cre recombinase." *Proc Natl Acad Sci USA* 92:160-164 (Jan. 1995).
Berridge and Fentress, "Disruption of natural grooming chains after striatopallidal lesions." *Psychobiology* 15(4):336-342 (1987).
Charité et al., "Ectopic Expression of *Hoxb-8* Causes Duplication of the ZPA in the Forelimb and Homeotic Transformation of Axial Structures." *Cell* 78:589-601 (Aug. 26, 1994).
Charité et al., "Regulation of the *Hoxb-8* Gene: Synergism between Multimerized *cis-* Acting Elements Increases Responsiveness to Positional Information." *Dev Biol* 171:294-305 (1995).
Chen, "Studies on the morphogenesis of the mouse stermun. III. Experiments on the closure and segmentation of the sternal bands." *J Anatomy* 87:130-149 (1953).
Chen, "Studies on the morphogenesis of the mouse sternum. I. Normal Embryonic Development." *J Anatomy* 86:373-401 (1952).
Chen and Capecchi, "Targeted Mutations in *Hoxa-9* and *Hoxb-9* Reveal Synergistic Interactions." *Dev Biol* 181(2):186-196 (1997).

Chisaka and Capecchi, "Regionally restricted developmental defects resulting from targeted disruption of the mouse homeobox gene *hox-1.5.*" *Nature* 350:473-479 (Apr. 11, 1991).
Condie and Capecchi, "Mice homozygous for a targeted disruption of *Hoxd-3* (*Hox-4.1*) exhibit anterior transformations of the first and second cervical vertebrae, the atlas and the axis." *Development* 119:579-595 (1993).
Condie and Capecchi, "Mice with targeted disruptions in the paralogous genes *hoxa-3* and *hoxd-3* reveal synergistic interactions." *Nature* 370:304-307(Jul. 28, 1994).
Davis et al., "Absence of radius and ulna in mice lacking *hoax-11* and *hoxd-11.*" *Nature* 375:791-795 (Jun. 29, 1995).
Deschamps and Wijgerde, "Two Phases in the Establishment of HOX Expression Domains." *Dev Biol* 156:473-480 (1993).
Dollé et al., "Coordinate expression of the murine *Hox-5* complex homoeobox-containing genes during limb pattern formation." *Nature* 342:767-772 (Dec. 14, 1989).
Fentress, "Expressive Contexts, Fine Structure, and Central Mediation of Rodent Grooming." *Ann NY Acad Sci* 525:18-26 (1988).
Fromental-Ramain et al., "*Hoxa-13* and *Hoxd-13* play a crucial role in the patterning of the limb autopod." *Development* 122:2997-3011 (1996).
Gavalas et al., "*Hoxa1* and *Hoxb1* synergize in patterning the hindbrain, cranial nerves and second pharyngeal arch." *Development* 125:1123-1136 (1998).
Goddard et al., "Mice with targeted disruption of *Hoxb-1* fail to form the motor nucleus of the VIIth nerve." *Development* 122:3217-28 (1996).
González-Reyes and Morata, "The Developmental Effect of Overexpressing a *Ubx* Product in Drosophila Embryos Is Dependent on Its Interactions with Other Homeotic Products." *Cell* 61:515-522 (May 4, 1990).

(Continued)

*Primary Examiner*—Jon P Weber
*Assistant Examiner*—Paul C. Martin
(74) *Attorney, Agent, or Firm*—Ballard Spahr Andrews & Ingersoll, LLP

(57) ABSTRACT

This invention provides in vivo and in vitro methods of screening for an agent or a combination of agents that reduces one or more repetitive behaviors, comprising contacting neuronal cells of an animal with a HOXB8 gene mutation with the agent combination of agents to be screened, and determining whether one or more repetitive behaviors of the animal is reduced or whether one or more biochemical correlates of repetitive behaviors is reduced, the reduction in one or more repetitive behaviors or biochemical correlates indicating an agent or combination of agents that reduces repetitive behaviors. The invention also provides method of treating a subject with repetitive behaviors, comprising administering a therapeutically effective dose of the agent or combination of agents identified by the screening method. Further provided is a population of animals with a HOXB8 gene mutation, wherein more than 30% of the animals have excessive grooming behaviors and wherein less than 10% of the animals show skeletal defects.

16 Claims, 8 Drawing Sheets

OTHER PUBLICATIONS

Graham et al., "The murine Hox-2 genes display dynamic dorsoventral patterns of expression during central nervous system development." *Development* 112:255-264 (1991).

Greer and Capecchi, "*Hoxb8* is Required for Normal Grooming Behavior in Mice." Neuron 33:23-34 (Jan. 3, 2002).

Horan et al., "Compound mutants for the paralogous *hoxa-4, hoxb-4*, and *hoxd-4* genes show more complete homeotic transformations and a dose-dependent increase in the number of vertebrae transformed." *Genes Dev* 9:1667-1677 (1995).

Ichimaru et al., "5-HT$_{1A}$-Receptor Subtype Mediates the Effect of Fluvoxamine, a Selective Serotonin Reuptake Inhibitor, on Marble-Burying Behavior in Mice." *Jpn J Pharmacol* 68(1):65-70 (May 1995).

Izpisua-Belmonte et al., "Expression of the homeobox *Hox-4* genes and the specification of position in chick wing development." *Nature* 350:585-589 (Apr. 18, 1991).

Le Mouellic et al., "Homeosis in the Mouse Induced by a Null Mutation in the *Hox-3.1* Gene." *Cell* 69:251-264 (Apr. 17, 1992).

Londei et al., "Investigative burying by laboratory mice may involve non-functional, compulsive, behaviour." *Behav Brain Res* 94:249-254 (Aug. 1998).

Maconochie et al., "Cross-regulation in the mouse *HoxB* complex: the expression of *Hoxb2* in rhombomere 4 is regulated by *Hoxb1*." *Genes Dev* 11: 1885-1895 (1997).

Mansour et al., "Disruption of the proto-oncogene *int-2* in mouse embryo-derived stem cells: a general strategy for targeting mutations to noon-selectable genes." *Nature* 336:348-352 (Nov. 24, 1988).

Morata, "Homeotic genes of *Drosophila*." *Curr Opin Genet Dev* 3:606-614 (1993).

Nelson et al., "Analysis of *Hox* gene expression in the chick limb bud." *Development* 122:1449-1466 (1996).

Neuteboom et al., "The hexapeptide LFPWMR in Hoxb-8 is required for cooperative DNA binding with Pbx1 and Pbx2 proteins." *Proc Natl Acad Sci USA* 92:9166-9170 (Sep. 1995).

Njung'e and Handley, "Evaluation of Marble-Burying Behavior as a Model of Anxiety." *Pharmacol Biochem Behav* 38(1):63-67(Jan. 1991).

Nohno et al., "Involvement of the *Chox-4* Chicken Homeobox Genes in Determination of Anteroposterior Axial Polarity during Limb Development." *Cell* 64:1197-1205 (Mar. 22, 1991).

Odenwald et al., "Expression of a homeo domain protein in noncontact-inhibited cultured cells and postmitotic neurons." *Genes Dev* 1:482-496 (1987).

Ogura and Evans, "Evidence for two distinct retinoic acid response pathways for *HOXB1* gene regulation." *Proc Natl Acad Sci USA* 92:392-396 (Jan. 1995).

Ogura and Evans, "A retinoic acid-triggered cascade of *HOXB1* gene activation." *Proc Natl Acad Sci USA* 92:387-391 (Jan. 1995).

Rancourt et al., Genetic interaction between *hoxb-5* and *hoxb-6* is revealed by nonallelic noncomplementation. Genes Dev. 9:108-122 (1995).

Rapoport et al., "Drug Treatment of Canine Acral Lick. An Animal Model of Obsessive-Compulsive Disorder." *Arch Gen Psychiatry* 49(7):517-521 (Jul. 1992).

Riddle et al., "Induction of the LIM Homeobox Gene *Lmx1* by WNT7a Establishes Dorsoventral Pattern in the Vertebrate Limb." *Cell* 83:631-640 (Nov. 17, 1995).

Sachs, "The Development of Grooming and Its Expression in Adult Animals." *Ann NY Acad Sci* 525:1-17 (1988).

Studer et al., "Genetic interactions between *Hoxa1* and *Hoxb1* reveal new roles in regulation of early hindbrain patterning." *Development* 125:1025-1036 (1998).

Thomas and Capecchi, "Site-directed Mutagenesis by Gene Targeting in Mouse Embryo-Derived Stem." *Cell* 51(3):503-512 (1987).

Valarche et al., "A 3' remote control region is a candidate to modulate *Hoxb-8* expression boundaries." *Int J Dev Biol* 41:705-714 (1997).

van den Akker et al., "Targeted inactivation of *Hoxb8* affects survival of a spinal ganglion and causes aberrant limb reflexes." *Mechan Dev* 89(3):103-114 (Sep. 1999).

Wolff et al., "Genetic aspects of obsessive-compulsive disorder." *Psychiatr Clin North Am* 23(3):535-544 (Sep. 2000).

Yan et al., "Ectopic Expression of hoxb2 After Retinoic Acid Treatment or mRNA Injection: Disruption of Hindbrain and Craniofacial Morphogenesis in Zebrafish Embryos." *Dev Dyn* 213:370-385 (1998).

Zwartkruis et al., "The murine *Hox-2.4* promoter contains a functional octamer motif." *Nucl Acids Res* 20(7):1599-606 (1992).

* cited by examiner

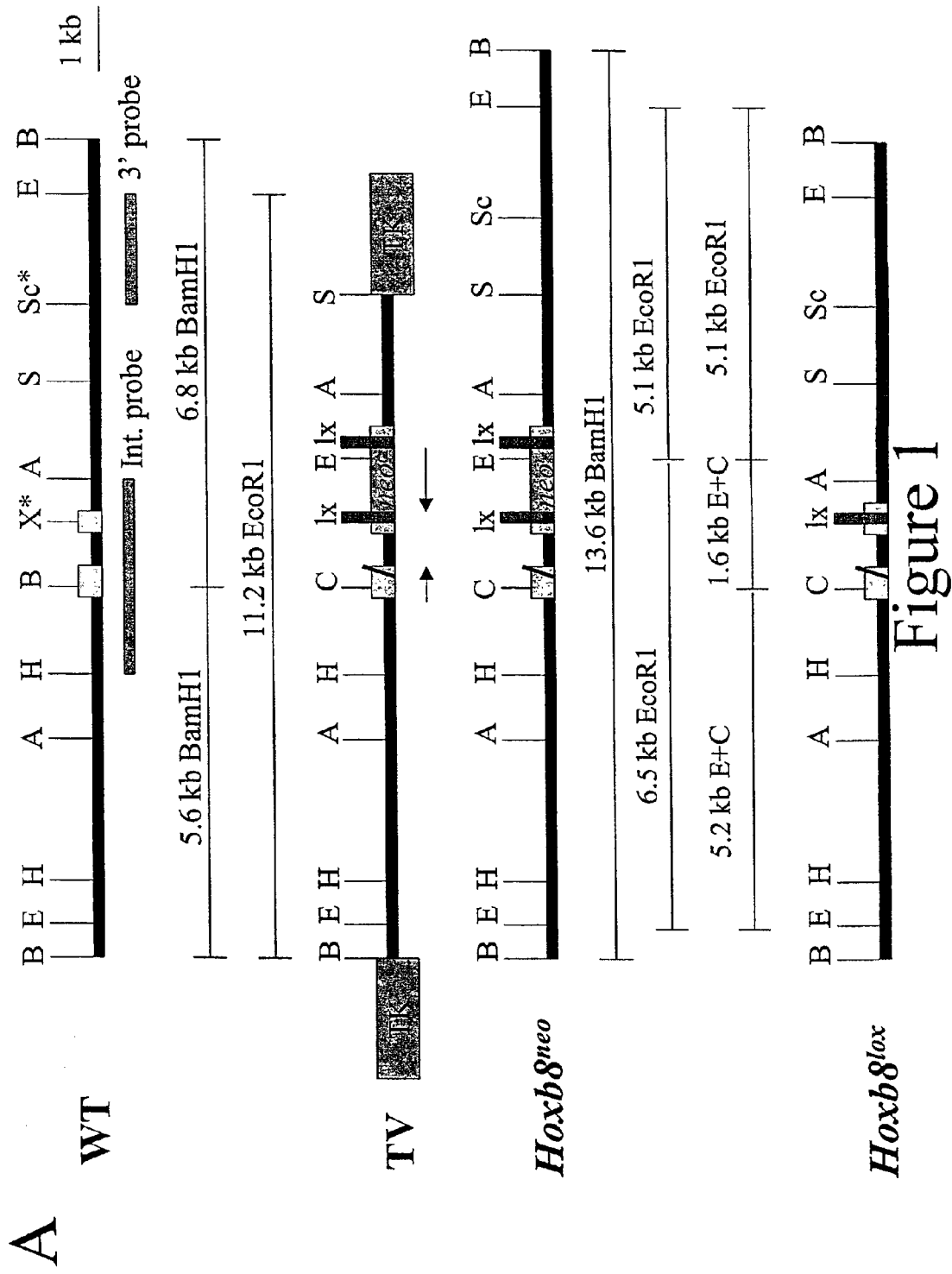

SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 1
cgaggccgcc agacctacag t                                              21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 2
catttactgc tgggaaactt gtct                                           24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 3
gcctgcttgc cgaatatcat gg                                             22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 4
tccagcaccc ttcgcaaatc c                                              21

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 5
gtgcccgctc cagcttctct t                                                 21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 6
gtaacaatgc catgttcaat                                                   20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 7
ctccatcgtg ggccgctcta g                                                 21
```

POPULATION OF HOXB8 MUTANTS AND USES IN IDENTIFYING AGENTS FOR TREATING REPETITIVE BEHAVIORS

This application claims priority to provisional U.S. patent application No. 60/295,494, filed May 31, 2001, which is incorporated herein by reference in its entirety.

This invention was made with government support under Grants 5R37 GM 21168 and 5 R01HD30701 awarded by The National Institutes of Health. The government has certain rights in the invention.

BACKGROUND OF THE INVENTION

1. Field of the Invention

This invention relates generally to uses of an animal model for repetitive behaviors, including symptoms of obsessive compulsive disorder and related behavioral disorders.

2. Background

Hoxb8 is a member of the mammalian Hox complex, a group of genes whose origins have been traced prior to the evolution of animal species. The Hox complex, or Homeobox-containing gene complex, comprises a group of 39 genes best known for their role in cuing positional information during embryogenesis. Like most Hox genes, Hoxb8 is first expressed at approximately E7.5 in the posterior region of developing embryos. During the next twenty-four hours, Hoxb8 expression continues to move anteriorly so that by E8.5 this gene is expressed to the level of somite 5 in the neuroectodenn and to the somite 10/11 boundary in the mesoderm. Later in development (E11.5), Hoxb8 is expressed in each of the developing spinal ganglia and throughout the spinal cord to the level of the hindbrain/spinal cord boundary (Deschamps and Wijgerde, 1993). Further studies have demonstrated that Hoxb8 expression in the spinal cord is restricted to portions of the dorsal and ventral halves of the developing cord (Graham et. al, 1991; van den Aklcer et. al., 1999). Within the prevertebra (PV), PV8 is the most anterior PV to express high levels of Hoxb8, although weak expression has been demonstrated in PV7. Additionally, Hoxb8 expression has been described in the zone of polarizing activity (ZPA) in the developing forelimb bud.

The colinear arrangement of genes within the Hox clusters of metazoan organisms has led to the speculation that this organization is an evolutionarily constrained requirement of Hox gene function. The sequential activation and maintenance of Hox gene expression in an ordered fashion that reflects the chromosomal position of each gene along the A-P axis of metazoan embryos, is determined through the concerted action of cis-acting regulatory sequences that govern expression of each gene (Gerhart and Kirschner, 1997). Since the protein-coding regions of Hox genes are often quite small, the vast majority of the sequences contained within Hox clusters are occupied by potential regulatory elements. These cis-regulatory networks appear to be responsible for the initial expression of Hox genes in a colinear fashion that reflects the order of genes on the chromosome, however, the precise mechanisms of Hox gene activation are not completely understood. The initial activation of Hox gene expression as a colinear single unit would provide an evolutionary advantage over systems requiring independent action to activate each individual gene, since fewer signals would be required for activation of the colinear network.

The Hox clusters have also acquired properties that are responsible for the maintenance of Hox protein expression networks along the A-P axis of metazoan embryos. Following initial activation of Hox gene expression, the continued expression of Hox genes throughout subsequent developmental stages is maintained by the Hox proteins themselves, through a variety of interactions with the cis-acting regulatory sequences within the cluster.

In developing metazoans, Hox gene expression begins in the posterior end of the embryo and then spreads anteriorly to reach sharp borders of expression along the A-P axis of embryos. As a consequence, the expression of many Hox genes is seen along the entire A-P axis posterior to their individual anterior limits of expression. This leads to overlapping expression of many Hox genes in posterior compartments. In order to limit the action of an individual Hox protein within the anterior-most compartment that it is expressed in, some Hox proteins have developed a hierarchy of repressive activity known as posterior prevalence or posterior dominance (Gonzalez-Reyes and Morata, 1990; Morata, 1993). In this hierarchy, a Hox protein that is expressed in a posterior compartment represses the expression of anterior genes within that same compartment. This property results in the sharpening of compartment boundaries in developing embryos, and even more importantly, is a consequence of Hox protein action within the Hox cluster. A second interesting feature that has been associated with the maintenance of Hox protein expression is autoactivation. Individual Hox proteins have been demonstrated to maintain their own expression within an individual segment following initial activation, by binding to and activating their own enhancers. For example, in mice autoregulation of the Hoxb1 locus has been demonstrated (Gavalas et al., 1998; Goddard et al., 1996; Maconochie et al., 1997; Ogura and Evans, 1995a; Ogura and Evans, 1995b; Studer et al., 1998; Yan et al., 1998).

Interestingly, after the initial establishment of compartment boundaries, the regionalization of cell types within individual compartments is independent of what is happening in other compartments. This is exemplified by the phenotypes associated by loss of Hox gene function. When an individual Hox gene is inactivated, in many instances the observed phenotypes are characterized by transformations to the identity of a neighboring compartment. However, even though the identity of a compartment may be altered, further activation and function of the rest of the Hox cluster is unaffected. As a consequence, in most instances, organisms mutant for an individual gene often display phenotypes associated with the compartment the gene is normally expressed in, however development of the rest of the embryo proceeds unaltered (Gerhart and Kirschner, 1997).

This compartmentalization of embryos following Hox gene activation has profound consequences with respect to the evolution of body patterns in metazoan organisms. Once the identity of a compartment has been determined through activation of the Hox network, the action of an individual Hox protein within a segment is determined by the interaction of the protein with the cis-regulatory sequences of the target gene. Throughout evolution, mutation and selection in the cis-acting regulatory sequences of potential target genes would have determined the regulatory interaction between a particular Hox protein and the target gene. As a consequence, interactions with different types of target genes within an individual segment may result, leading to changes in the both the appearance and function of that segment in developmentally mature metazoans. Thus, the varied body patterns that result from the identical segmental location and expression of orthologous Hox proteins in different metazoa may be the result of the evolutionary conservation of a flexible developmental program.

During vertebrate evolution, quadruplication of the Hox cluster resulted in an increase in both the amount of Hox protein present in an individual compartment, as well as the number of cis-acting regulatory sequences controlling Hox gene expression. Paralogous Hox proteins that were expressed in the same compartment may have been able to activate and repress one another, since they probably shared common regulatory sequences. Consequently, vertebrate paralogous Hox genes have diverged in two ways: through changes in the cis-acting regulatory sequences and through changes in the protein coding sequences. Changes in the cis-acting regulatory sequences may have produced changes in the amount of a particular protein present or altered the location or timing of expression for the individual gene. Changes in the protein-coding sequences could have resulted in alterations in the specificity of the homeodomain for DNA, as well as alterations in interactions with other proteins. As a result of changes in both the cis-acting regulatory sequences and protein coding sequences, a single member of a paralogous group could evolve interactions with its own set of target genes, thereby producing novel morphologies within a compartment.

Previous analyses of both the expression pattern and function of Hoxb8 had suggested that this gene was crucial to the development of forelimb buds (Deschamps and Wijgerde, 1993). In the developing forelimb bud, the posterior margin, the zone of polarizing activity (ZPA), is characterized by expression of Sonic hedgehog (Shh) and the 5' Hoxd genes (Dolle et al., 1989; Nelson et al., 1996). Transplantation of either the ZPA or Shh-secreting cells to the anterior margin of the limb bud results in mirror-image expression patterns of the 5' Hoxd genes, as well as mirror-image digit patterns (Izpisua-Belmonte et al., 1991; Nohno et al., 1991; Riddle et al., 1995). Expression of Hoxb8 in the developing forelimb is restricted to the posterior half of the structure. Ectopic expression of Hoxb8 using the retinoic acid receptor-s promoter to drive expression in regions anterior to the normal limit of Hoxb8 expression resulted in the expression of Shh in the anterior portion of the limb bud (Charite et al., 1994). Furthermore, these Hoxb8 transgenic mice also developed a second ZPA in the anterior portion of the forelimb bud that was characterized by expression of the 5' Hoxd genes, resulting in the formation of mirror-image duplications of the forelimbs. These experiments suggested that Hoxb8 played a crucial role in the establishment of the ZPA and thus the patterning of the posterior half of the forelimb bud.

Although expression of Hox genes other than Hoxb8 in adult tissues, including the CNS, have been described, most studies assessing Hox protein function have been limited to embryological studies. Consequently, whether the activity of Hox proteins in adult tissues results from conserved interactions or through novel interactions is unknown. Previous analyses of the cis-regulatory elements surrounding the Hoxb8 gene have indicated that expression of this gene is governed by the concerted action of numerous enhancer elements (Charite et al., 1995; Valarche et al., 1997; Zwardtlis et al., 1992). Prior to the present invention, a role for the expression product of Hoxb8 in the central nervous system or in complex behaviors such as grooming behaviors have never been elucidated.

Obsessive-compulsive disorder (OCD) is a condition that is characterized by obsessions such as fear of contamination and/or such repetitive behaviors as excessive cleanliness. Epidemiological studies using cross-national representations have indicated that this disorder is quite common, with a prevalence rate ranging from 1.9-2.5 per 100 in seven different international communities (Horwath and Weissman, 2000). A genetic component for this disorder is suggested by twin studies, where concordance rates as high as 87% between monozygotic twins have been reported. Additionally, family studies have indicated rates of OCD as high as 10.9% in first-degree relatives of OCD probands (Wolff et al., 2000).

Repetitive behaviors are also associated with other disorders such as Tourette syndrome, which is characterized by repetitive tics and utterances, and trichotillomania, which is characterized by the removal of one's own body hair. The national Tourette Syndrome Association, Inc. used to publish estimates suggesting that Tourette syndrome affected only 1 in every 10,000 people. More recent evidence, however, evidence suggests that 2 to 3 out of every 100 children or teenagers may have some form of this spectrum disorder. In the case of trichotillomania, there have been no epidemiological studies to identify the actual number of people with this condition yet. It is estimated that in the United States alone, there are probably between 6 to 8 million sufferers of trichotillomania.

Despite the prevalence of repetitive behaviors, few animal models exist to facilitate the study of the underlying basis for or treatments of such behaviors. Proposed animal models include dogs with canine acral lick dermatitis (Rapoport, et al., 1992), a condition in which the animal licks its paws or flank to a point that ulcers and infection develop, or other animals that show displacement behaviors, such as grooming, upon stress. (Moon-Fanelli et al., 1999; Fentress, 1988; Sachs, 1988) Finally, normal behaviors such as marble burying in wild-type mice have been used as models for repetitive behaviors. (Londei et al. 1998; Ichimaru, 1995; Njung'e and Handley, 1991) Prior to the present invention, however, no genetic model for repetitive behavior.

SUMMARY OF THE INVENTION

In accordance with the purpose(s) of this invention, as embodied and broadly described herein, this invention, in one aspect, relates to an in vivo method of screening for an agent or combination of agents that reduces one or more repetitive behaviors, comprising contacting neuronal cells of an animal with a HOXB8 gene mutation with the agent or combination of agents to be screened, and determining whether one or more repetitive behaviors of the animal is reduced, the reduction in one or more repetitive behaviors indicating an agent or combination of agents that reduces repetitive behaviors. The invention also relates to an in vitro method of screening for an agent or combination of agents that reduces one or more repetitive behaviors, comprising contacting neuronal cells of an animal with a HOXB8 gene mutation with the agent or combination of agents to be screened, and determining whether one or more biochemical correlates of repetitive behaviors of an animal is reduced, the reduction in one or more repetitive behaviors indicating an agent or combination of agents that reduces repetitive behaviors.

The invention also relates to a method of treating a subject with repetitive behaviors, comprising administering a therapeutically effective dose of the agent or combination of agents identified by the screening method.

In another aspect, the invention relates to a population of animals with a HOXB8 gene mutation, wherein more than 30% of the animals have excessive grooming behaviors and wherein less than 10% of the animals show skeletal defects.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 2A shows the amount of time each animal spent engaged in the activity. FIG. 2B shows no difference between Hoxb8 mutants and their control sib pairs in the average amount of time spent engaged in this behavior.

FIG. 3A shows the amount of time each animal spent engaged in grooming activity. FIG. 3B shows the average time the Hoxb8 mutants and their control siblings spent grooming during a 12 hour period. The Hoxb8 mutant animals were found to spent almost twice as much time engaged in grooming behaviors compared to their control siblings.

FIG. 5A shows the amount of time each animal spent sleeping. FIG. 5B shows the average amount of time for mutants and control animals. Mutant animals spent on average one hour less sleeping compared to control siblings.

DESCRIPTION OF THE PREFERRED EMBODIMENTS

Figure 1:
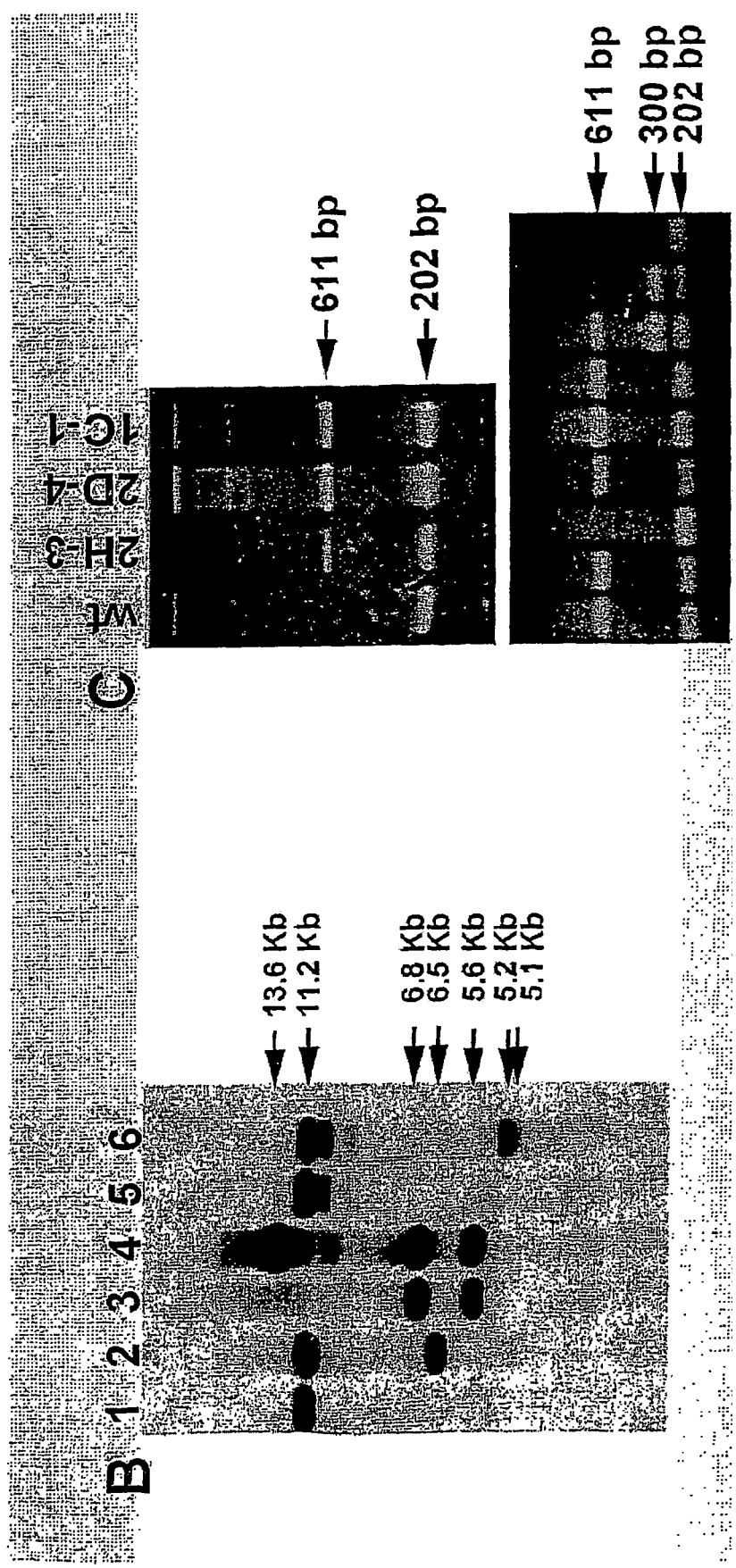
FIG. 1A shows a schematic of the wild-type and mutant alleles. (A). Representations of the Hoxb8 genomic locus (WT), the targeting vector (TV), the Hoxb8$^{neo}$ allele, and the Hoxb8$^{lox}$ allele. The two exons of Hoxb8 are represented as yellow boxes, the neo$^r$ gene by the blue box, and the lox sites are shown in purple. The arrows indicate the direction of transcription for Hoxb8 and the neo$^r$ gene. The diagonal line in the first exon represents the introduced translational stop site. The location of the two probes used to screen ES cell lines are shown in gray. The restriction digests and subsequent fragment lengths used to identify homologous recombinants are shown below the wild type and Hoxb8$^{neo}$ alleles. A, Asp 718; B, BamH1; C, Cla1; E, EcoR1; H, HindIII; 1x, lox; S, Sal1; Sc, Sac1; X, Xmn1. * indicates that multiple sites exist and are not all represented.
FIG. 1B shows a Southern blot of three homologous recombinants generated by the insertion of a floxed pMC-1neo$^r$ cassette into the homeodomain, electroporation into R1 ES cells, and positive-negative selection to enrich for cells containing the Hoxb8 disruption. The recombinants were identified by analysis using a 3' flanking probe, an internal probe, and restriction digests based on the presence of an introduced site in the first exon.
FIG. 1C shows genotype analysis of progeny generated by intercross matings of progeny created when the selection cassette was removed via injection of pMC-1Cre into the male pronucleus of eggs fertilized by Hoxb8$^{neo}$ male heterozygotes. The progeny were genotyped by PCR assays using tail DNA.

Before the present compounds, compositions, articles, devices, and/or methods are disclosed and described, it is to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an agent" includes combinations or mixtures of various agents, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

By the term "therapeutically effective amount" of a compound as provided herein is meant a nontoxic but sufficient amount of the compound to provide the desired regulation of the gene expression or regulation of a particular repetitive behavior. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained.

"Eliciting," "modulating," "regulating," selective gene expression is intended to mean that a compound is capable of acting as an activator or an antagonist of gene expression, either directly or indirectly. For example, gene expression could be regulated at the level of DNA transcription or translation.

In one embodiment, the present invention provides a method of screening for an agent or combination of agents that reduces one or more repetitive behaviors. The screening method comprises the steps of contacting neuronal cells of an animal with a HOXB8 gene mutation with the agent or combination of agents to be screened, and determining whether one or more repetitive behaviors of the animal is reduced. The reduction in one or more repetitive behaviors indicates an agent or combination of agents that reduces repetitive behaviors.

The agent or combination of agents used in the screening method may be used in a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that may be used in conjunction with the preparation of formulations of the agents and which is incorporated by reference herein.

By "repetitive behaviors" is meant any number of repetitive compulsive-like behaviors, including excessive grooming behaviors. Such repetitive actions in human have been described in Diagnostic and Statistical Manual of Mental Disorders, ed 4, 1994 (DSM-IV)) and include excessive hand washing, excessive bathing and other ritualistic behaviors, some of which are aimed at cleanliness (DSM-IV). Repetitive actions in animals are similar and include mutilatory biting and picking of their skin, as well as pulling and plucking of their hair. Such repetitive behaviors can be self directed or can be directed toward others. By "excessive grooming behaviors" is meant a significantly higher incidences or duration of grooming behaviors as compared to control. The significantly higher amount can include an increase of 10%, 20%, 30%, 40%, 50%, 60%, 70%, 80%, 90%, 100% or greater, or any amount in between.

Thus, in various embodiments of the screening method, the reduction in one or more repetitive behaviors comprises a reduction in one or more excessive grooming behaviors. For example, in one embodiment, the excessive grooming behavior comprises a reduction in the total amount of time the animal grooms. In another embodiment, the reduction in excessive grooming behavior comprises a reduction in the total number of times the animal initiates grooming. In another embodiment, the reduction in excessive grooming behavior comprises a reduction in hair removal caused by grooming. In yet another embodiment, the reduction in excessive grooming behavior comprises a reduction in lesions caused by grooming. The reduction in excessive grooming behavior comprises either a reduction in self-grooming, a reduction in grooming of other animals, or both.

The reduction in one or more repetitive behaviors can be determined in a variety of ways. For example, the animal to be tested could be observed or videotaped before and after the agent is administered, or the animal to be tested could be observed or videotaped after the agent is administered and compared to untreated animals with the same mutation. The number of repetitive behaviors before and after administration could be compared or the total amount of time engaged in the repetitive behavior could be determined.

The excessive grooming behaviors demonstrated in the animal to be screened can be non-induced or induced. By "induced" is meant that a causative agent that provokes grooming is used. Causative agents include, for example, stress or application of a stimulus to the animal's skin or coat. For example, a water mist applied to a rodent induces grooming.

By "contacting" is meant an instance of exposure of at least one neuron or neuronal cell to an agent. As used herein, the contacting step can be in vivo, e.g., where behavioral assessments of repetitive behaviors are used, or in vitro, e.g., when changes at the cellular level are assessed In vitro screening methods could include isolation and molecular characterization of individual neuronal phenotypes and screening of these specific cells types for biochemical changes that correlate with reduced repetitive behaviors in the whole animal. The screening assay could include high throughput analysis using microarrays and proteonomics.

In in vitro screening methods, the cell can be contacted with an agent, for example, by adding the agent to the culture medium (by continuous infusion, by bolus delivery, or by changing the medium to a medium that contains the agent). In in vivo screening methods, the cell is contacted by adding the agent to the extracellular fluid of the neuronal cell (by orally, parenterally (e.g., intravenously), intramuscularly, intraperitoneally, topically, transdermally, locally, systemically, intraventricularly, intracerebrally, subdurally, or intrathecally administering the agent to be screened). Depending upon the agent to be screened and the mode of administration, one skilled in the art would recognize that the blood brain barrier may diminish or prevent access to neurons when administered systemically. One skilled in the art would know to modify the mode of administration, the pharmacologic carrier, or other parameters to circumvent restrictions posed by the blood brain barrier.

One method of in vivo administration is the use of microosmotic pumps (e.g., Alzet® pump). The pumps can be placed under the animals skin with a cannula extending into the subdural or intraventricular space.

The duration of "contact" with a cell or group of cells is determined by the time the agent is present at physiologically effective levels or at presumed physiologically effective levels in the medium or extracellular fluid bathing the cell or cells. Such duration of contact varies based on the half-life of the agent. The contacting step in vivo can be by bolus delivery or by continuous infusion.

The neuronal cell contacted in the screening method may or may not be a Hoxb8 expressing cell. Given the structure of neuronal circuitry, the pharmacologic effect of an agent may be upstream or downstream of a Hoxb8 expressing cell. For example, an agent that reduces repetitive behaviors could affect a serotonergic neuron which synapases with a Hoxb8 expressing cell.

By "a HOXB 8 gene mutation" is meant any mutation in the HOXB8 gene that results in a decrease in gene function. A decrease in gene function includes a decrease in transcription or expression. Such a mutation includes a nonsense mutation or a mutation that results in a hypomorphic allele.

The animal with the HOXB8 gene mutation is preferably a transgenic mouse, but can be any laboratory animal in which similar gene manipulation can be accomplished using techniques well known in the art. Preferably the mutation is achieved by point mutation rather than by the introduction of exogenous DNA, for example, using the lacZ fusion method.

The invention also provides a population of animals with a HOXB8 gene mutation, wherein more than 30% of the animals have excessive grooming behaviors and wherein less than 10% of the animals show skeletal defects. The skeletal defects include patterning defects in the axial skeleton, like rib mutations (e.g., partial to fall fusion of two or more ribs, absence of all or part of one or more ribs, bifurcation of ribs).

In the preferred embodiment, the HOXB8 gene mutation is a point mutation produced by gene targeting and is not a mutation that introduces exogenous DNA.

In another embodiment, more than 50% of the population of animals with the HOXB8 gene mutation show excessive grooming behaviors. In another embodiment, 75% of the animals show excessive grooming behaviors. In yet another embodiment, 100% of the animals show excessive grooming behaviors. The excessive grooming behaviors of the animals of the population comprise an increased total amount of time the mutant animal grooms as compared to animals lacking the mutation, an increased total number of times the mutant animal initiates grooming as compared to animals lacking the mutation, an increased hair removal caused by the mutant animal's grooming as compared to animals lacking the mutation, increased lesions caused by the mutant animal's grooming as compared to animals lacking the mutation, increased self-grooming, and/or increased mutant animal grooming of other animals. The excessive grooming behavior of the population of animals can be non-induced or induced.

The invention also provides a method of treating a subject with repetitive behaviors, comprising administering to the subject a therapeutically effective dose of the agent or combination of agents identified by the screening method of the invention. The repetitive behaviors being treated include, for example, compulsive behaviors. The repetitive behaviors of the subject may be symptoms of an obsessive compulsive disorder, Tourette's syndrome, trichotillomania, autism, disorders of mental delay (e.g., mental retardation) or other disorders or syndromes marked by repetitive actions such as those described in Diagnostic and Statistical Manual of Mental Disorders, ed 4, 1994 (DSM-IV).

The agents identified by the screening method of the invention may be conveniently formulated into pharmaceutical compositions composed of one or more of the compounds in association with a pharmaceutically acceptable carrier. The compounds may be administered orally, parenterally (e.g., intravenously), intramuscularly, intraperitoneally, topically, transdermally, locally, systemically, intraventricularly, intracerebrally, subdurally, or intrathecally. Depending upon the agent to be screened and the mode of administration, special provisions may be required to promote the agent to cross the blood brain barrier. One skilled in the art would know to modify the mode of administration, the pharmacologic carrier, or other parameters to circumvent restrictions posed by the blood brain barrier. The amount of active compound administered will, of course, be dependent on the subject being treated, the subject's weight, the manner of administration and the judgment of the prescribing physician.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see *Remington's Pharmaceutical Sciences*, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parental administration, if used, is generally characterized by injection. Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

For topical administration, liquids, suspension, lotions, creams, gels or the like may be used as long as the active compound can be delivered to the surface of the skin.

The present invention also provides a method of screening for a genetic mutation associated with repetitive behaviors in a subject comprising acquiring from the subject a genetic sample and comparing that genetic sample with a genetic profile associated with a manifestation of repetitive behaviors. In an preferred embodiment, the genetic profile reflects a nonsense mutation or hypomorphic allele of the HOXB8 gene.

Experimental

The following examples are put forth so as to provide those of ordinary skill in the art with a complete disclosure and description of how the compounds, compositions, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

EXAMPLE 1

Generation of Hoxb8$^{neo}$ Mutant Mice

An 11.2 kb DNA fragment that contained the Hoxb8 gene was isolated from a genomic DNA library prepared using mouse 129Sv ES cell line DNA, and used to construct the Hoxb8 targeting vector. In order to generate a true null allele, two different mutations were introduced into the Hoxb8 locus. The first mutation is a frameshift mutation resulting in a premature translational stop codon within the first exon (FIG. 1A). The second mutation is an insertion of a floxed pMC-1neo$^r$ cassette into the homeodomain. The targeting vector was electroporated into R1 ES cells, followed by positive-negative selection to enrich for cells containing the Hoxb8 disruption (Thomas and Capeechi, 1987; Mansour et al., 1988). Southern blot analysis using a 3' flanking probe, an internal probe, and restriction digests based on the presence of an introduced site in the first exon were used to identify three homologous recombinants (FIG. 1B). Two of these cell lines were microinjected into C57B1/6 blastocysts to generate chimeric males that passed the mutations through the germline, giving rise to the Hoxb8$^{neo}$ colony. Intercross matings generated mice homozygous for the Hoxb8$^{neo}$ mutation at normal Mendelian ratios. Removal of the selection cassette was accomplished via injection of pMC-1Cre (Araki et al., 1995) into the male pronucleus of eggs fertilized by Hoxb8$^{neo}$ male heterozygotes (FIG. 1C). Intercross matings between resulting progeny were used to generate the Hoxb8$^{lox}$ colony. All subsequent progeny of both colonies were genotyped by PCR assays using tail DNA (FIG. 1C). Removal of the neo insert was not required to produce the excessive grooming behavior described below. The behavior was fully penetrant in both the neo and the lox colonies.

EXAMPLE 2

Genotype Analysis

Pups and newborns were genotyped by PCR analysis of tail DNA (Thomas, 1992); embryos were genotyped via PCR analysis of yolk sac DNA (Carpenter et al., 1993). PCR primers were derived from within the Hoxb8 homeobox (5' primer, Hoxb8), sequences at the 3' end of the neo$^r$ gene (3' primer, neo$^r$) and sequences near the 3' end of the Hoxb8 gene (3' primer, Hoxb8). The sequence of each of the primers is as follows: 5'Hoxb8-5'CGAGGCCGCCAGACCTACAGT3' (SEQ ID NO:1); 3'Hoxb8-5'CATTTACTGCTGGGAAACTTGTCT3' (SEQ ID NO:2); 3'neo$^r$-5'GCCTGCTTGCCGAATATCATGG3' (SEQ ID NO:3). The PCR reactions were carried out under the following cycling conditions; 95° C. for 30 seconds (sec), 60° C. for 20 sec, 72° C. for 60 sec, for 28 cycles followed by a single cycle of 72° C. for seven min.

EXAMPLE 3

Skeletal Phenotype

Numerous studies have demonstrated that loss of function of an individual Hox gene often results in patterning defects of the axial skeleton. (E.g., Chen and Capecchi, 1997; Condie and Capecchi, 1993 and 1994; Davis et al., 1995; Fromental-Ramain et al.1996; Horan et al., 1995). To determine if Hoxb8 is required for appropriate patterning during bone morphogenesis, skeleton preparations of homozygous mutant newborn pups from both the Hoxb8$^{neo}$ and Hoxb8$^{lox}$ colonies were examined.

In wild-type mice, the first rib normally is formed as a ventrolateral projection that originates from the sclerotome adjacent to the first thoracic vertebra. This rib articulates with the top of an independently formed sternum (Chen 1952, 1953). Examination of 62 Hoxb8$^{neo}$ homozygous mutants revealed a defect in the formation of the first rib in 46 (74%) of the mutants. This defect was bilateral in 75% of the mutants examined. The expressivity of the defect ranged from a relatively mild form in which the first and second ribs fused near their attachment point at the sternum, to a severe defect characterized by complete absence of a rib adjacent to the first thoracic vertebra. In mutants in which the first rib did not form or was shortened, bifurcation of the second rib was observed.

No defects in the formation of the first rib were found in skeleton preparations of 35 Hoxb8$^{lox}$ homozygous mutants. The only difference between these two colonies is the presence of the neo$^r$ gene in the homeodomain of Hoxb8$^{neo}$ mice. The introduced stop codon in the first exon of both colonies should produce the same effect with respect to loss of function of Hoxb8. The other phenotypes associated with loss of Hoxb8 function that are discussed in this report have been identified with 100% penetrance in both colonies. It is assumed that the rib phenotype that was observed in the Hoxb8$^{neo}$ mutants results from the presence of the neo$^r$ gene and not from loss of Hoxb8 function.

EXAMPLE 4

Misexpression of Hoxb6 and Hoxb9 in Hoxb8 Mutants

Previous examination of homozygous mutant animals carrying mutations at either the Hoxb6 or the Hoxb9 locus had revealed defects in the formation of the first thoracic rib associated with loss of function of each of these genes (Rancourt, 1995; Chen and Capecchi, 1997). Since the rib defects observed in the Hoxb8$^{neo}$ homozygotes resembled those described in Hoxb6 and Hoxb9 mutant animals, the expression pattern of both genes was examined in Hoxb8 mutants. At E9.5 the anterior limit of expression of both Hoxb6 and Hoxb9 is at the level of PV8 in the somites of wild-type embryos. In situ hybridization of six E9.5 Hoxb8$^{neo}$ mutant embryos revealed an alteration in the wild-type expression pattern in 2 (30%) of the mutants. On the other hand, 66% (6/9) of E9.5 Hoxb8$^{neo}$ mutant embryos displayed an alteration from the wild-type expression pattern of Hoxb9. In embryos displaying aberrant expression patterns, expression of the gene analyzed was shifted posteriorly by one somite, from the level of PV8 to the level of PV9. This alteration was not observed in E9.5 Hoxb8$^{neo}$ heterozygotes, Hoxb8$^{lox}$ heterozygotes or Hoxb8$^{lox}$ homozygotes. No disruption of the wild-type expression pattern of Hoxb-9 was observed in E10.5, E11.5, or E12.5 Hoxb8$^{neo}$ homozygous mutants.

Since the expression pattern of two genes in close proximity to Hoxb8 were found to be altered in the Hoxb8$^{neo}$, but not the Hoxb8$^{lox}$ mutant embryos it was possible that the neo$^r$ gene interfering with the wild-type expression patterns of neighboring genes. In situ hybridization was used to demonstrate that the neo$^r$ gene is expressed in E9.5 Hoxb8$^{neo}$ hetero- and homozygous mutant embryos (data not shown). The expression pattern of neo$^r$ gene resembled a Hox like pattern along the antero-posterior axis. Homozygous mutant embryos showed stronger expression than heterozygotes indicating a possible quantitative difference. No expression was observed in wild-type or Hoxb8$^{lox}$ hetero- and homozygous controls.

EXAMPLE 5

Hair Removal Phenotype

Due to the presence neo$^r$ gene in the genome of the Hoxb8$^{neo}$ colony, all further discussions of phenotypic analysis will refer to the Hoxb8$^{lox}$ colony only. During maintenance of the colonies, it was observed that all of the homozygotes from both colonies displayed large bald patches on their lateral and ventral body surfaces. The degree of hair loss varies from mildly affected mice that simply display bald spots, to the most severely affected animals that contain open lesions. Examination revealed a significant amount of body hair trapped in the gums and teeth, as well as the stomach, of the mutant mice. This finding indicated that the mutant mice were actively removing the hair.

EXAMPLE 6

Analysis of Skin

To determine if the mice were able to react to external stimuli, the animals were tested for their ability to sense heat and cold, hard and soft pressure, as well as pain. All of the mice displayed normal reactions when tested, indicating a normal range of sensation in the mutant mice. In addition, immunostaining of E9.5 embryos with anti-neurofilament antibody and adult skin sections with PGP9.5 failed to demonstrate any differences in the amount of peripheral nerve innervation in the Hoxb8 mutants.

Histological analysis of skin from mutant mice demonstrated a thickening of the epidermis when compared with wild-type littermates, however this thickening was only observed in older mice that had displayed some degree of hair removal (n=20). When the skin from two and three-week old control and mutant littermates (n=18 for each stage) was examined, no differences were observed. This indicates that the thickening of the epidermis observed in affected mice is the result of the hair removal, and not the cause.

Physical examination of the skin did not reveal any redness or inflammation in the area where hair had been removed except in areas containing lesions. In addition, neither Giemsa staining nor histological analysis of sldn from mutant animals revealed evidence of lymphocyte and granulocyte infiltration or mast cell degranulation, thus an inflammatory reaction is not stimulating the mice to remove their hair.

EXAMPLE 7

Home Cage Behavioral Analysis

To determine the conditions under which the Hoxb8 mutant mice were losing their body hair, fourteen control and mutant sib pairs (8 male; 6 female), each in their own home cage, were placed in a locked room and videotaped individually using a JVC camcorder and VCR for a single 24-hour period. Animals were housed in clear cages on a standard 12 hour light/dark cycle with water and chow available at all times. Videotapes were changed every eight hours.

Twelve hours of videotape, broken up into three four-hour blocks spread evenly throughout the day, were examined for each animal and scored for displays of innate behaviors including eating, drinking, sleeping, and grooming. During analysis of the videotapes, an individual grooming bout was recorded only if the bout contained all of the elements of a grooming sequence, lasted at least 30 seconds, and did not contain a pause of greater than 15 seconds. Analysis of the videotapes of Hoxb8 mutants and their control siblings in their home cages revealed a number of interesting findings.

Figure 2:
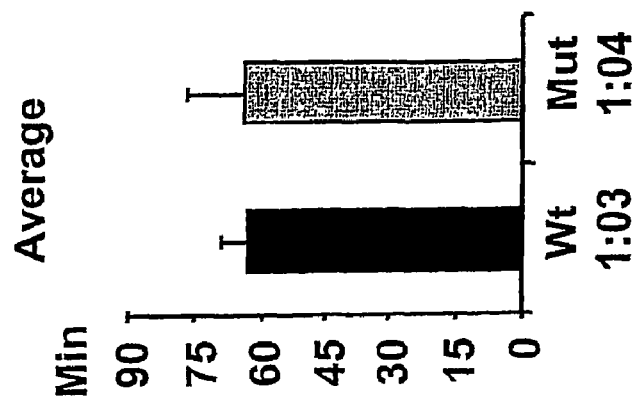
FIG. 2 shows a comparison of the eating behaviors of Hoxb8 mutants and their control sib pairs.
Figure 2:
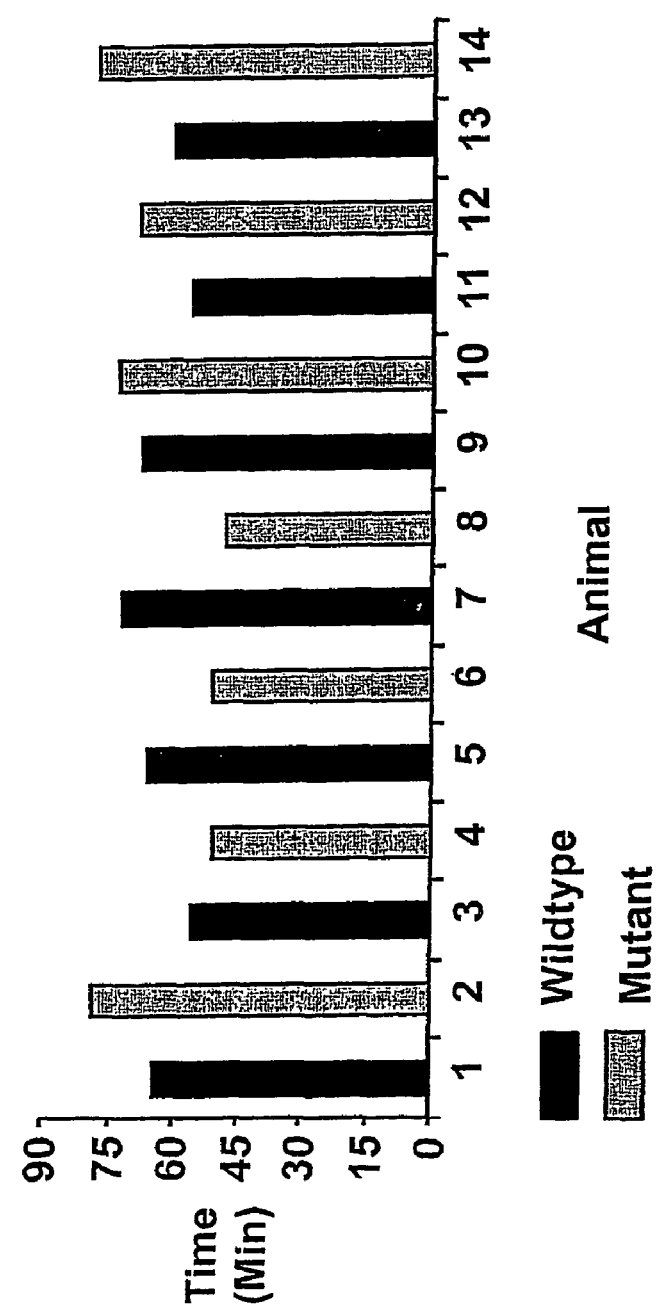

While in their home cage, mice generally engage in numerous periods of activity, characterized by exploration of the cage that is interspersed with eating and drinking. These periods of activity are alternated with periods of resting and/or sleeping in the nest. In this environment, the animals often perform grooming behaviors as a transitional behavior between extended periods of rest and activity (Fentress, 1988). Comparison of the eating behaviors of Hoxb8 mutants and their control sib pairs failed to reveal any differences in the average amount of time spent engaged in this behavior (FIG. 2). Not only was there no difference in the average amount of time eating when mutants and controls were compared, but also there was no difference in the number of times the mutant animals initiated eating bouts when compared to controls. With respect to drinking behaviors, the Hoxb8 mutant animals were observed to not have any difficulties with drinking, and were not found to spend excessive amounts of time drinking.

Although the amount of time spent engaged in exploratory behaviors was not determined, it was noted that the Hoxb8 animals visited all regions of their cages during the analysis periods. Additionally, the Hoxb8 animals were observed to climb on both the water bottle and the wire top, as well as hang from and move the length of the cage using the wire top. Rearing was also often observed, and nest-building behaviors appeared normal.

Figure 3:
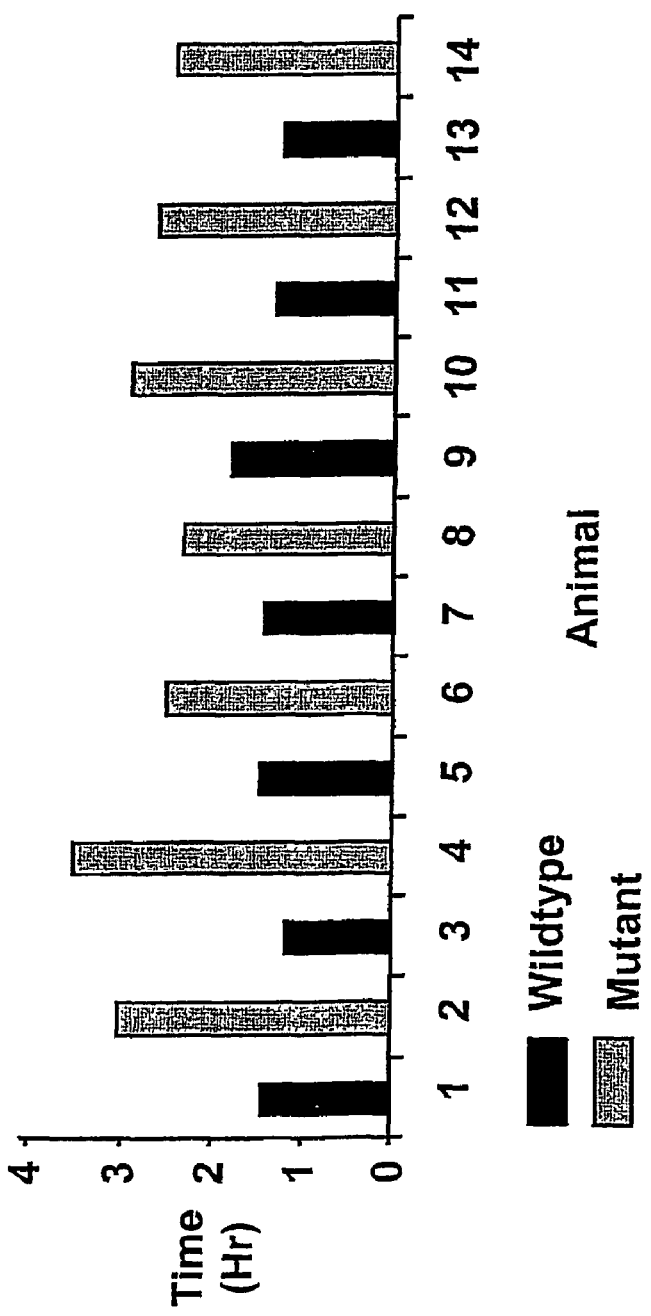
FIG. 3 shows a comparison of home cage grooming behaviors of Hoxb8 mutants and their control siblings.
Figure 3:
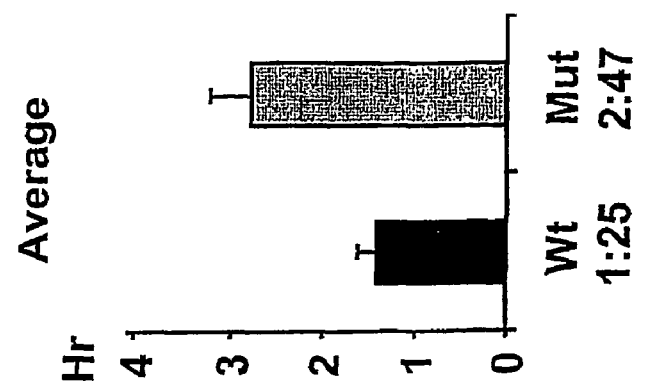
Figure 4:
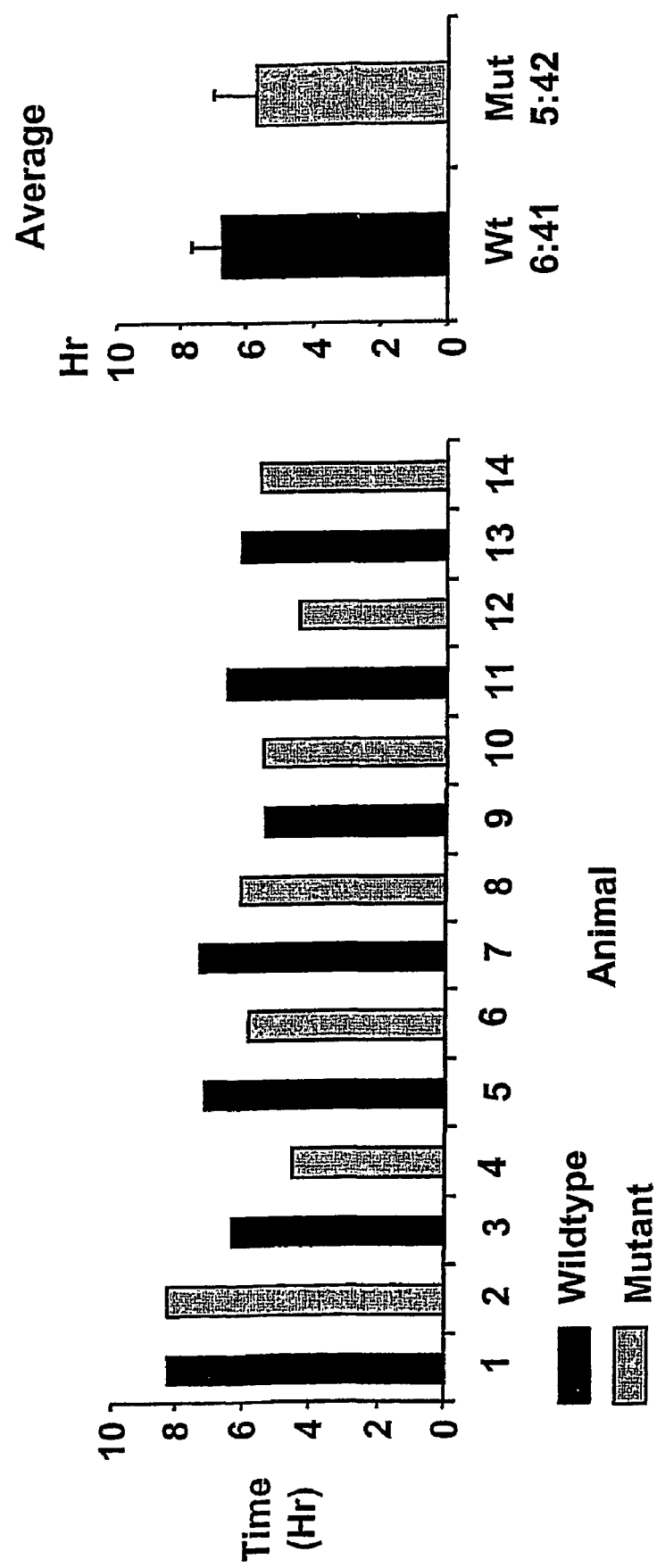
FIG. 4A demonstrates the total number of grooming bouts initiated, as well as the duration of each bout, for each animal during a single 4-hour observation period.
FIG. 4B shows the total number of times grooming bouts were initiated for either the wild type or mutant animals during the 4-hour observation period.

In contrast, when home cage grooming behaviors were analyzed, significant differences were found between the Hoxb8 mutants and their control siblings (FIG. 3). When the total amount of time the animals spent grooming during the 12 hours of tape analyzed was calculated, the Hoxb8 mutant animals were found to spend almost twice as much time engaged in grooming behaviors compared to their control siblings. Additionally, when a side by side comparison of grooming bouts during a given time period is made, a second difference is evident. The mutant animals initiate grooming sequences much more frequently than control animals (FIG. 4). Although the mutant animals were found to spend more time engaged in grooming behaviors, it should be noted that the grooming sequences observed occurred within a normal context, i.e. as a transitional behavior between periods of rest and activity. Extended periods of activity were not interrupted by grooming. Additionally, the individual grooming bouts that were analyzed demonstrated that the mutant animals groomed all regions of their body, and did not appear to have any difficulties performing grooming actions.

Figure 5:
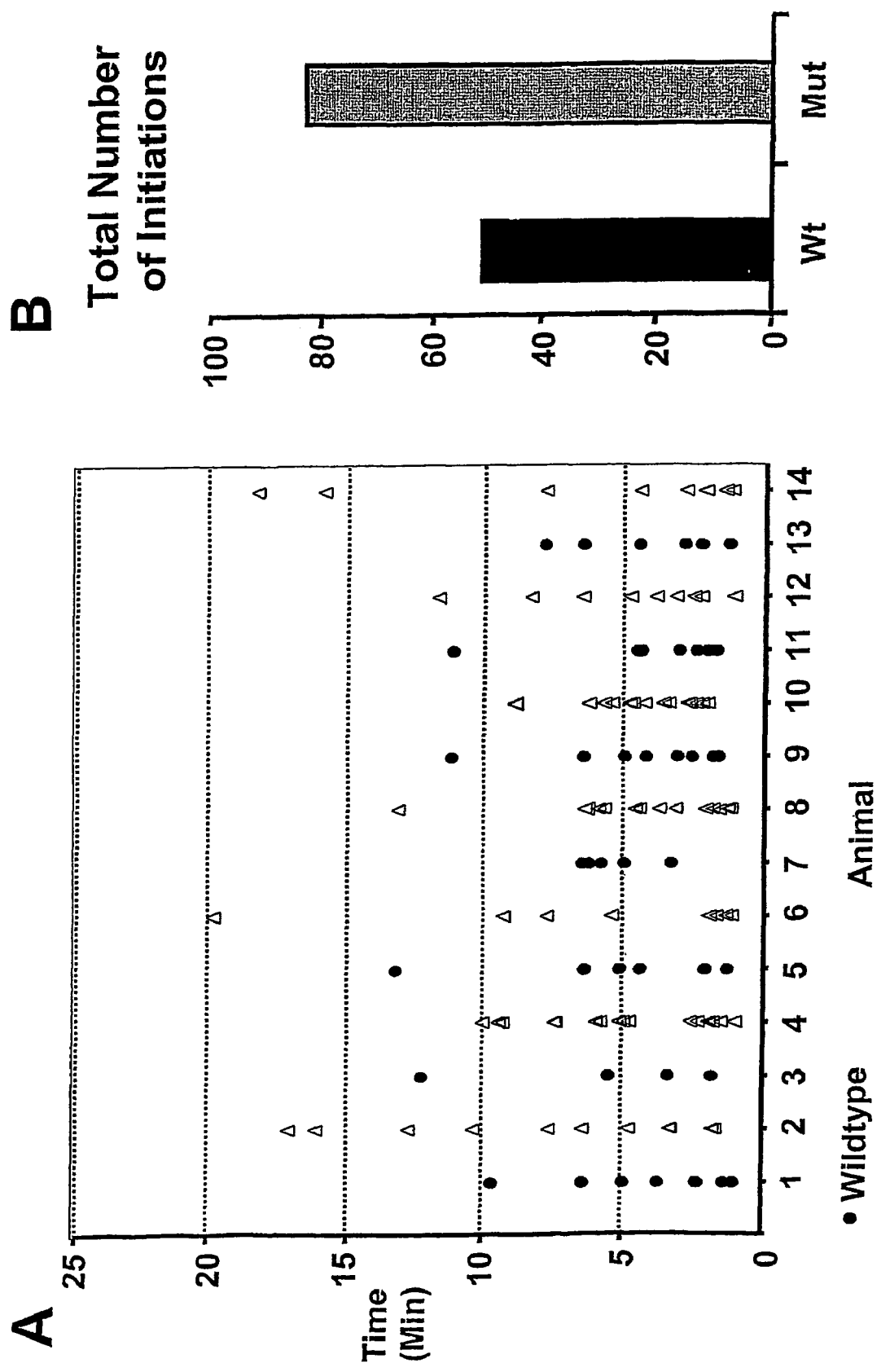
FIG. 5 shows the total amount of time Hoxb8 mutants spent sleeping during the twelve hour analysis period as compared to their control siblings.

Calculation of the amount of time spent sleeping during the twelve hour analysis period revealed that mutant animals spend on average one hour less sleeping compared to control siblings (FIG. 5). Since long periods of grooming generally precede periods of rest, it was felt that the difference in the amount of time spent resting/sleeping most likely is a consequence of the excessive grooming behavior.

EXAMPLE 8

Appearance of Symptoms of Excessive Grooming

The age that symptoms of the excessive grooming behavior first appear varies from animal to animal, however symptoms generally appear during adolescence. The earliest age at which mutilation has been observed is within a week of weaning (approximately 4 weeks); however, all of the mutant mice display at least some degree of hair removal prior to twelve weeks of age. The mutant mice will continue to remove their body hair throughout their lifetime, and most create an open lesion. Affected areas are found anywhere on the body that the mouse can reach while grooming. One interesting note is that in order for proper development of secondary sexual characteristics in male mice, as well as during arousal and following sexual activity, appropriate autogrooming must occur (reviewed by Sachs, 1988). Some of the male Hoxb8 mutant mice described in this study will groom themselves so vigorously that they will move the penal sheath, a flap of skin that normally houses the penis in mice.

EXAMPLE 9

Hoxb8 Excessive Grooming Includes a Social Component

In addition to the excessive autogrooming that has been described, a social component of the behavior was also observed. When Hoxb8 mutant mice are housed with control littermates, the control animals are often found to display large bald patches on their backs and the tops of their heads. Interestingly, the whiskers and facial regions of the control mice do not appear to be excessively groomed. Since the area of hair removal is often found on areas that are not accessible to the control mouse, homecage videotape analysis of Hoxb8 mutants housed with control littermates was used to demonstrate that the bald patches found on the control animals were the consequence of excessive grooming by Hoxb8 mutants.

EXAMPLE 10

Induced Grooming Analysis

Figure 6:
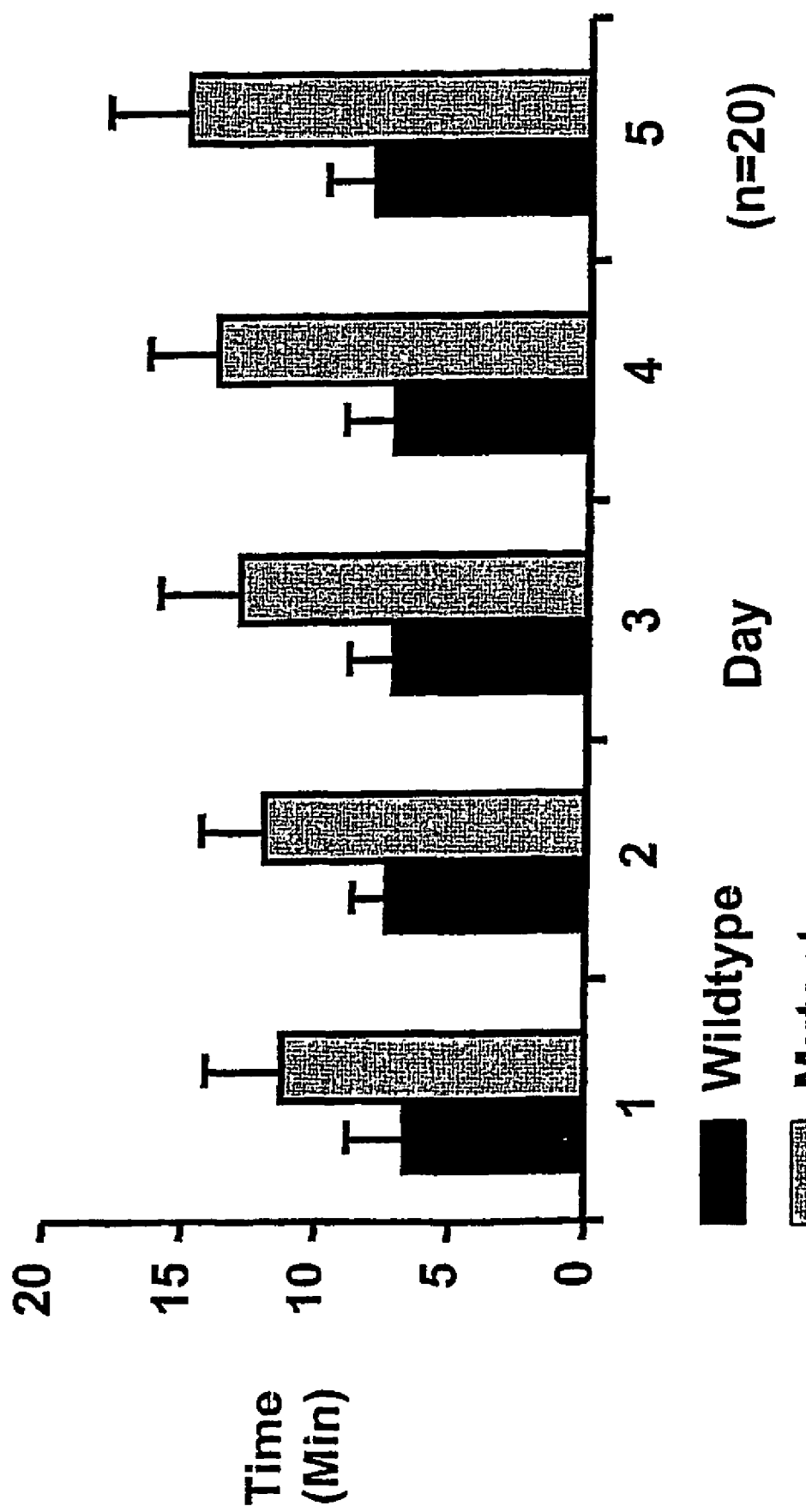
FIG. 6 shows the average amount of time Hoxb8 mutant mice spent in induced grooming behaviors on five consecutive days as compared to controls. Grooming was induced by misting the animals with water. Immediately after misting, the animals were videotaped for twenty minutes on five consecutive days while in a clear cage lacking bedding, food, or water. The Hox mutants spent approximately twice as much time engaged in induced grooming behaviors compared to controls.

Previous studies of rodent grooming behaviors have demonstrated that misting with water will stimulate grooming behaviors (Berridge, et al., 1987b). To determine if the Hoxb8 mutant mice groomed excessively under these conditions, ten control and mutant sib pairs were each placed in individual cages that did not contain bedding, food, or water. Following a ten-minute acclimation period, the animals were lightly misted with water, and videotaped for a period of twenty minutes. This assay was repeated each day for five consecutive days. The videotapes were analyzed, and the amount of time each animal spent engaged in grooming behaviors was recorded. The average amount of time control animals and mutant animals spent grooming was calculated for each day. Analysis of the induced grooming study demonstrated again that the Hox mutants spent approximately twice as much time engaged in grooming behaviors compared to controls (FIG. 6).

EXAMPLE 11

Behavior Analysis in a Second Genetic Background

Figure 7:
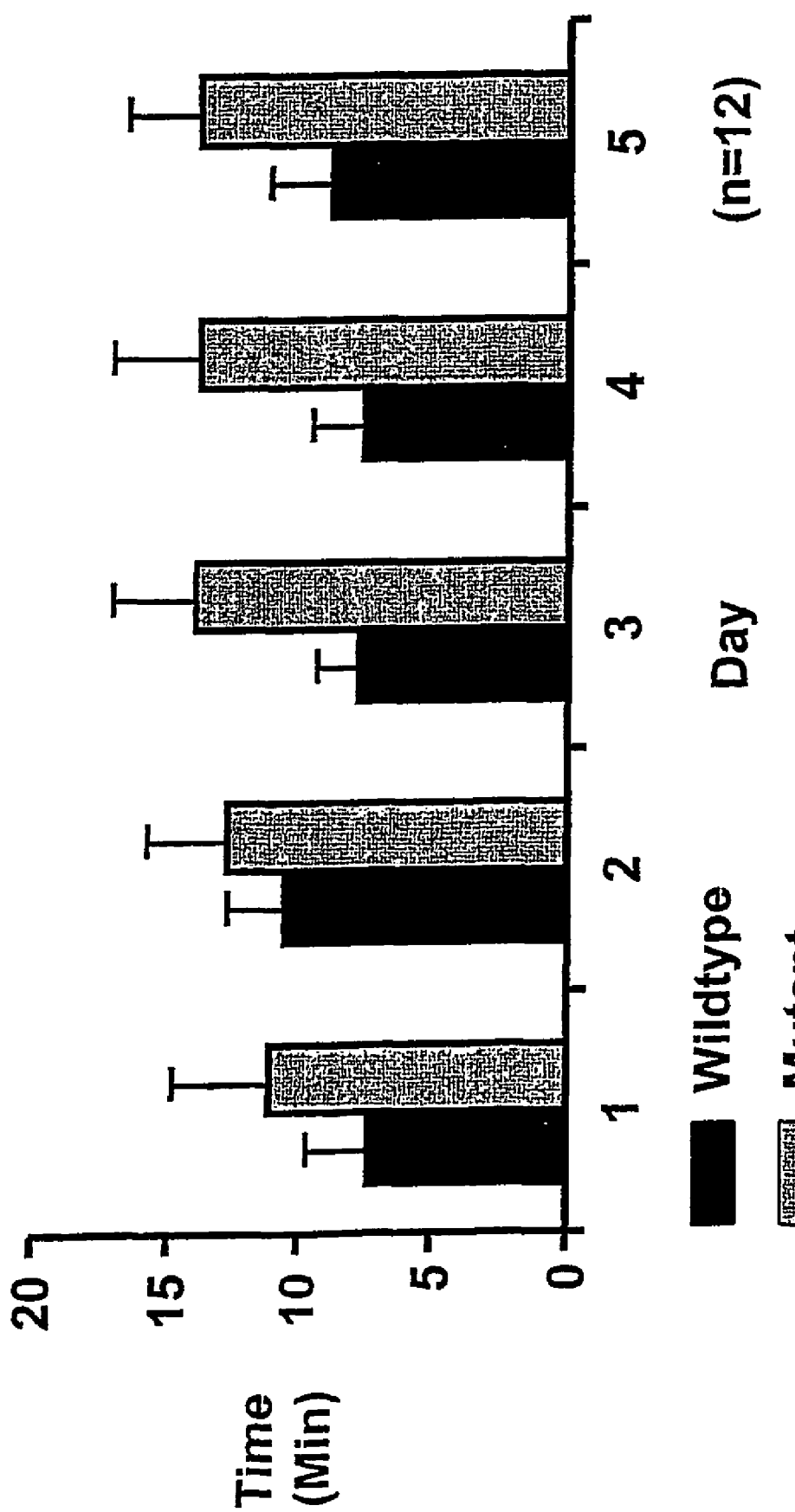
FIG. 7 shows the amount of time spent in induced grooming behaviors by mice bred by backcrossing the F1 generation mutants to an outbred strain of mice (Swiss-Webster) for five generations. When twelve animals were tested using the induced grooming assay, the homozygous mutants were observed to spend approximately twice as much time grooming on each of the five days tested, when compared to control siblings.

Finally, to ensure that this particular Hox gene was responsible for the excessive behavior, we backcrossed our mutation from the F1 generation (B16/Sv129) of mice to an outbred strain of mice (Swiss-Webster) for five generations. In the outbred strain, we were still able to characterize the excessive grooming behavior in all of the homozygous mutants using both the home cage and the induced grooming assays. Indeed, when twelve animals were tested using the induced grooming assay, the homozygous mutants were once again found to spend approximately twice as much time grooming on each of the five days tested, when compared to control siblings (FIG. 7). Additionally, visual inspection of the animals allows for easy identification of homozygous mutant animals since all remove a portion of their body hair and some self-mutilate in this genetic background as well.

EXAMPLE 12

Detection of Hoxb8 Transcripts

For the RT-PCR assay, animals were sacrificed via $CO_2$ asphyxiation, and the brain and cervical spinal cord rapidly dissected. Further dissection separated the cervical spinal, the medulla and pons, from the rest of the adult brain. Following dissection, each tissue was placed in an eppendorf tube containing tissue resuspension buffer (Qiagen RNeasy Kit®) and broken up using a sterile disposable pestle. The samples were further disrupted using Qia Shredder™ and total RNA samples were subsequently isolated using the Qiagen RNeasy Mini Kit Mini Kit®. Amplification of Hoxb8 transcripts was performed using the PCR Access Kit (Promega). 100 ng of total RNA was used for each reaction, and the sequence of the primers used to amplify either Hoxb8 or the actin control are as follows: 5'RTb8-5'TCCAGCACCCTTCGCAAATCC3' (SEQ ID NO:4); 3'RTb8-5'GTGCCCGCTCCAGCT-TCTCTT-3' (SEQ ID NO:5); 5'Actin-5'GTAACAATGC-CATGTTCAAT3' (SEQ ID NO:6); 3'Actin-5'CTC-CATCGTGGGCCGCTCTAG (SEQ ID NO:7). Amplification conditions were the same as previously described.

Although Hox genes are primarily known for their role in specifying segmental identity during embryogenesis, some studies have described expression patterns for Hox transcripts in adult animals (Hoxa5 and Hoxc8). (Odenwald et al., 1987; Le Mouellic et al., 1992). To determine whether Hoxb8 is expressed in the adult animal, an RT-PCR assay, using primers that flank both of the mutations was developed. As demonstrated in FIG. 3, the expected 542 bp fragment was amplified from the cervical spinal cord, the brainstem, and the anterior brain in 16-week old wild-type animals. Interestingly, when this RT-PCR assay was tested using RNA isolated from the entire brain of adult Hoxb8 homozygous mutant animals, a 580 bp fragment representing the Hoxb8 mutant allele (a 34 bp lox site plus a 4 bp insertion at the BamH1 site), was amplified. Fragments of both sizes were amplified when brains were dissected from heterozygous animals. Additionally, both the 542 bp and the 580 bp fragments were subdloned and sequenced. The 542 bp fragment was identical in sequence to that reported for Hoxb8 (Genbanlc Acc. No.: X13721), whereas the 580 bp fragment was found to contain both of the mutations that were introduced into the Hoxb8 locus. These results demonstrate two very important findings. First, Hoxb8 is expressed within the CNS of adult mice, and second, the cells that are responsible for generating this signal are present in the adult CNS of Hoxb8 mutants.

EXAMPLE 13

Cellular Localization of HoxB8

In an attempt to elucidate the molecular nature of the excessive grooming behavior observed in the Hoxb8 mutants, we have analyzed a number of tissues. Analyses of the skeleton, skin, peripheral, and central nervous systems failed to reveal any obvious structural abnormalities associated with improper patterning to explain the observed behavior.

To determine the cellular localization of Hoxb8 in the adult brain, animals were asphyxiated using $CO_2$ and fixed via cardiac perfusion with cold 4% paraformaldehyde (PFA). Following perfusion, the brain and spinal cord were dissected and post-fixed for at least six hours in 4% PFA. Samples were then transferred to a 1×PBS solution containing 5% sucrose for cryopreservation.

The samples were cryopreserved for multiple days at 4° C. while gradually increasing the sucrose concentration to 30%. The tissue was then frozen in OCT, sectioned at 10 □m, and mounted onto SuperfrostPlus® slides (VWR).

Embryos were harvested from staged pregnancies, and fixed overnight in 4% PFA. Following fixation, the embryos were prepared for freezing as described above, frozen in OCT, and sectioned at 10 μm. The slides were dried at room temperature overnight, and stored at −70°.

To detect Hoxb8 transcripts in sections of embryos and adult brains, the slides were warmed to room temperature (RT) and rehydrated by washing twice in a calcium and magnesium free (CMF) 1×PBS solution, followed by treatment with proteinaseK (1 ug/ml in CMF-PBS) for ten minutes at RT. The slides were then rinsed 3× with CMF-PBS and refixed in 4% PFA for twenty minutes on ice. Next, the slides were washed with CMF-PBS, and deacetylated with 0.25% acetic anhydride/0.1M triethanolamine for 10 minutes with stirring, followed by a wash with 0.2×SSC for 10 minutes, again with stirring. The slides were then dehydrated in an ethanol (EtOH) series and allowed to air dry for 30 minutes. Hybridization buffer (50% formamide/2×SSC/10% Dextran sulfate/0.01% herring sperm DNA/0.02% SDS) was spread across the sections, the slides were coverslipped, and subsequently prehybridized for 2-3 hours (hr) at 50° C. Following prehybridization, the Hoxb8 riboprobe was diluted in hybridization buffer (0.5 μg/ml) and placed on the sections. The slides were then heated to 85° C. for 10 minutes, and hybridized overnight at 55° C. in a chamber made humid by a solution containing 50% formamide/4×SSC. The next day the slides were washed first with 4×SSC/10 mM DTT for 1 hr at RT, followed by 50% fortnamide/2×SSC/10 mM DTT (30 min; 50° C.), and 500 mM NaCl/10 mnM Tris-HCl, pH 7.4/1 mM EDTA (NTE) for 15 minutes at 37° C. Next, unbound RNA was removed using 10 μg/ml RNase A (Sigma) in NTE (30 min; 37° C.), and the slides were washed with NTE (2×15 min; 37° C.). Finally, the slides were washed with 2×SSC (15 min; RT), and 0.1×SSC (15 min; RT). Following a brief rinse in 100 mM Tris-HCl, pH7.5/150 mM NaCl (TS), the samples were blocked with 5% normal sheep serurn/0.03% Triton X-100 in TS for 30 min at RT. The secondary antibody (α-dig-gold) was diluted 1:400 in 10% sheep serum/0.3%Triton in TS, placed on the sections, and the slides were incubated o/n at 4° C. The next morning the slides where washed with 100 MM Tris-HCl, pH 7.4/150 mM NaCl/0.1% fish gelatin (3×5 min), post-fixed in 2% gluteraldehyde (2 min), and subsequently washed with $dH_2O$ (5×; 30 sec), and then $ddH_2O$ (3×3 min) followed by incubation with the Silver Enhancing Kit (Ted Pella) for 20 min. The reaction was stopped using 2.5% Na-thiosulfate, and the slides were rinsed thoroughly in running water. The sections were then counterstained with hematoxylin, dehydrated with an EtOH series, and coverslipped. In order to determine the cellular localization of Hoxb8 within the adult CNS, in situ hybridization using an antisense riboprobe from the 3' untranslated region of Hoxb8 was performed on adult brain sections (Chen and Capecchi, 1997). Hoxb8 expression was found in a number of regions within the CNS, including the olfactory bulb, the cortex, the hippocampus, the basal ganglia, the cerebellum, and the brain stem. In the olfactory bulb, Hoxb8 expression was strongest in cells within the mitral cell layer. A few Hoxb8 expressing cells were also seen within the external plexiform layer and the granule cell layer. This pattern of expression was not seen when a "sense-strand" probe was hybridized to the sections.

Within the hippocampus, Hoxb8 expression was restricted to the pyramidal cell layer in the CA1-CA3 region and the granule cell layer of the dentate gyrus. Once again this pattern of expression is not present when the sense probe is hybridized to the sections. The cerebral cortex also contains Hoxb8 expressing cells within layers 2-6. Although this expression pattern extends throughout the entire cortex, the region with the strongest expression is the frontal cortex. The caudate-putamen (neostriaturm) region of the basal ganglia also contains Hoxb8 expressing cells. Within the cerebellum, Hoxb8 expression can be localized to both Purkinge cells and basket cells. And in the brain stem, Hoxb8 is expressed in cells throughout the reticular formation as well as cells in the cranial ganglia. Examination of Hoxb8 expression on adult brain sections from both hetero- and homozygous mutant animals resulted in an expression pattern that is identical to the wild-type expression pattern.

EXAMPLE 14

Effect of Prozac on Repetitive Behaviors of Hoxb8 Mutants

The selective serotonin reuptake inhibitor (SSRI) class of pharmacological agents has previously shown efficacy in the reduction of obsessive-compulsive behaviors in humans, as well as some forms of excessive behavior in veterinary models (use the DSM-IV reference and the reference to veterinary models and implications for trichotillomania). In an attempt to attenuate the excessive grooming behavior observed in the Hoxb8 mutant animals, fifteen sib pairs of wild type and Hoxb8 mutant animals were treated with the SSRI Fluoxetine-HCl (Flu) (brand name Prozac). An additional set of fifteen sib pairs were treated with vehicle alone to serve as controls. The animals were housed individually on a standard light cycle and had both food and water available at all times. Prior to treatment, each of the animals was subjected to the induced grooming assay (see Example 10) and the time each animal spent grooming was calculated.

Each animal was treated with 10 mg/kg/day Flu or vehicle alone delivered using Alzet mini-osmotic pumps (Alza Corp. model #2004) implanted subdurally on the backs of the animals. Following thirty days of treatment with either Flu or vehicle each of the animals was again subjected to the induced grooming assay. A number of the mutant animals that had received Flu treatment exhibited signs of hair regrowth indicating the Flu treatment had some efficacy.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. AraKi, K., Araki, M., Miyazaki, J-I. and Vassalli, P. (1995). Site-specific recombination of a transgene in fetilized eggs by transient expression of Cre recombinase. Proc. Natl. Acad. Sci. USA 92, 160-164.
2. Berridge, K. C. and Fentress, J. C. (1987b). Disruption of natural grooming chains after striatopallidal lesions. Psychobiology 15, 336-342.
3. Charite, J., de Graaff, W., Shen, S., and Deschamps, J. (1994). Ectopic expression of Hoxb-8 causes duplication of the ZPA in the forelimb and homeotic transformation of axial structures, Cell 78, 589-601.
4. Charite, J., de Graaff, W., Vogels, R., Meijlink, F., and Deschamps, J. (1995). Regulation of the Hoxb-8 gene:

synergism between multimerized cis-acting elements increases responsiveness to positional information, Dev Biol 171, 294-305.

5. Chen, J. M. (1953). Studies on the morphogenesis of the mouse sternun. III. Experiments on the closure and segmentation of the sternal bands. Journal of Anatomy 87, 130-149.

6. Chen, J. M. (1952). Studies on the morphogenesis of the mouse sternum. Journal of Anatomy 86, 373-401.

7. Chen, F., Capecchi, M. R. (1997). Targeted mutations in hoxa-9 and hoxb-9 reveal synergistic interactions. Dev Biol 181(2):186-96

8. Chisaka, O., and Capecchi, M. R. (1991). Regionally restricted developmental defects resulting from targeted disruption of the mouse homeobox gene hox-1.5, Nature 350, 473-9.

9. Condie, B. G., and Capeechi, M. R. (1993). Mice homozygous for a targeted disruption of Hoxd-3 (Hox-4.1) exhibit anterior transformations of the first and second cervical vertebrae, the atlas and the axis, Development 119, 579-95.

10. Condie, B. G., and Capecchi, M. R. (1994). Mice with targeted disruptions in the paralogous genes hoxa-3 and hoxd-3 reveal synergistic interactions, Nature 370, 304-7.

11. Davis, A P, Witte, D P, Hsieh, H M, Potter, S S and Capecchi, M R (1995) Absence of radius and ulna in mice laclcing hoxa1 and hoxd11. Nature 375, 791-5.

12. Deschamps, J., and Wijgerde (1993). Two phases in the establishment of hox expression domains. Developmental Biology 156, 473-480.

13. Diagnostic and Statistical Manual of Mental Disorders, ed 4, (1994) (DSM-IV).

14. Dolle, P., Izpisua-Beimonte, J. C., Falkenstein, H., Renucci, A., and Duboule, D. (1989). Coordinate expression of the murine Hox-5 complex homoeobox-containing genes during limb pattern formation, Nature 342, 767-72.

15. Fentress, J. C. (1988). Expressive contexts, fine structure, and central mediation of rodent grooming. Annals of the New York Academy of Sciences 525, 18-26.

16. Fromental-Ramain, C., Warot, X., Messadecq, N., LeMeur, M., Dolle, P., and Chambon, P. (1996). Hoxa-13 and Hoxd-13 play a crucial role in the patterning of the limb autopod, Development 122, 2997-3011.

17. Gavalas, A., Studer, M., Lumsden, A., Rijli, F. M., Krumlauf, R., and Chambon, P. (1998). Hoxa1 and Hoxb1 synergize in patterning the hindbrain, cranial nerves and second pharyngeal arch, Development 125, 1123-36.

18. Gerhart, I., and Kirschner, M. (1997). Cells, embryos, and evolution: toward a cellular and developmental understanding of phenotypic variation and evolutionary adaptability (Malden, Mass., Blackwell Science).

19. Goddard, J. M., Rossel, M., Manley, N. R., and Capecchi, M. R. (1996). Mice with targeted disruption of Hoxb-1 fail to form the motor nucleus of the VIIth nerve, Development 122, 3217-28.

20. Gonzalez-Reyes, A., and Morata, G. (1990). The developmental effect of overexpressing a Ubx product in Drosophila embryos is dependent on its interactions with other homeotic products, Cell 61, 515-22.

21. Graham, A., Maden, M., and Krumlauf, R. (1991). The murine Hox-2 genes display dynamic dorsoventral patterns of expression during central nervous system development. Development 112, 255-264.

22. Horan, G. S., Ramirez-Solis, R., Featherstone, M. S., Wolgemuth, D. J., Bradley, A., and Behringer, R. R. (1995). Compound mutants for the paralogous hoxa-4, hoxb-4, and hoxd-4 genes show more complete homeotic transformations and a dose-dependent increase in the number of vertebrae transformed, Genes Dev 9, 1667-77.

23. Ichimaru Y, Egawa T, Sawa A. (1995 May) 5-HT1A-receptor subtype mediates the effect of fluvoxamine, a selective serotonin reuptake inhibitor, on marble-burying behavior in mice.Jpn J Pharmacol. 68(1):65-70.

24. lzpisua-Belmnonte, J. C., Tickle, C., Dolle, P., Wolpert, L., and Duboule, D. (1991). Expression of the homeobox Hox-4 genes and the specification of position in chick wing development, Nature 350, 585-9.

25. Le Mouellic, H., Lallemand, Y., and Brulet, P. (1992). Homeosis in the mouse induced by a null mutation in the Hox-3.1 gene, Cell 69, 251-64.

26. Londei T, Valentini A M, Leone V G. (1998 Aug) Investigative burying by laboratory mice may Involve non-functional, compulsive, behaviour. Behav Brain Res. 94(2): 249-54.

27. Maconochie, M. K., Nonchev, S., Studer, M., Chan, S. K., Popperl, H., Sham, M. H., Mann, R. S., and Krumlauf, R. (1997). Cross-regulation in the mouse HoxB complex: the expression of Hoxb2 in rhombomere 4 is regulated by Hoxb1, Genes Dev 11, 1885-95.

28. Mansour, S. L., Thomas, K. R., Capecchi, M. R. (1988). Disruption of the proto-oncogene int-2 in mouse embryo-derived stem cells: general strategy for targeting mutations to noon-selectable genes, Nature 336(6197:348-52.

29. Moon-Fanelli, A. A., Dodman, N., O'Sullivan, R. L.: *Veterinaiy models of compulsive self-grooming: Parallels with trichotillomania.* In Trichotillomania (ed. Stein, D., Christenson, G A, Hollander, E) American Psychiatric Press, Washington, D.C., 1999).

30. Morata, G. (1993). Homeotic genes of Drosophila, Curr Opin Genet Dev 3, 606-14.

31. Nelson, C. E., Morgan, B. A., Burke, A. C., Laufer, E., DiMambro, E., Murtaugh, L. C., Gonzales, E., Tessarollo, L., Parada, L. F., and Tabin, C. (1996). Analysis of Hox gene expression in the chick limb bud, Development 122, 1449-66.

32. Njung'e K, Handley SL. (1991 Jan) Evaluation of marble-burying behavior as a model of anxiety. Pharmacol Biochem Behav. 38(1):63-7.

33. Nohno, T., Noji, S., Koyarna, E., Ohyama, K., Myokai, F., Kuroiwa, A., Saito, T., and Taniguchi, S. (1991). Involvement of the Chox-4 chicken homeobox genes in determination of anteroposterior axial polarity during limb development, Cell 64, 1197-205.

34. Odenwald, W. F., Taylor, C. F., Palmer-Hill, F. J., Friedrich, V., Tani, M., and Lazzarini, R. A. (1987). Expression of a homeo domain protein in noncontact-inhibited cultured cells and postnitotic neurons, Genes Dev 1, 482-96.

35. Ogura, T., and Evans, R. M. (1995a). Evidence for two distinct retinoic acid response pathways for HOXB1 gene regulation, Proc Natl Acad Sci U S A 92, 392-6.

36. Ogura, T., and Evans, R. M. (1995b). A retinoic acid-triggered cascade of HOXB1 gene activation, Proc Natl Acad Sci U S A 92, 387-91.

37. Rancourt, D. E., Tsuzuli, T., and Capecchi, M. R. (1995). Genetic interaction between hoxb5 and hoxb6 is revealed by nonallelic noncomplementation. Genes and Development 9, 108-122.

38. Rapoport, J. L., Ryland, D. H., Kriete, M. (1992). Drug treatment of canine acral lick. An animal model of obsessive-compulsive disorder, Arch Gen Psychiatry 49(7):517-21.

39. *Remington's Pharmaceutical Sciences*, latest edition, by E. W. Martin Mack Pub. Co., Easton, Pa.

40. Riddle, R. D., Ensini, M., Nelson, C., Tsuchida, T., Jessell, T. M., and Tabin, C. (1995). hiduction of the LIM homeobox gene Lmxl by WNT7a establishes dorsoventral pattern in the vertebrate limb, Cell 83, 631-40.
41. Sachs, B. D. (1988). The development of grooming and its expression in adult animals. Annals of the New York Academy of Sciences 525, 1-17.
42. Studer, M., Gavalas, A., Marshall, H., Ariza-McNaughton, L., Rijli, F. M., Chambon, P., and Krmnlauf, R. (1998). Genetic interactions between Hoxal and Hoxb1 reveal new roles in regulation of early hindbrain patterning, Development 125, 1025-36.
43. Thomas, K. R. and Capecchi, M. R. (1987). Site-directed mutagenesis by gene targeting in mouse embryo-derived stem, Cell 51(3):503-12.
44. Valarche, I., de Graaff, W., and Deschamps, J. (1997). A 3' remote control region is a candidate to modulate Hoxb-8 expression boundaries, Int J Dev Biol 41, 705-14.
45. van den Akker, E., Reijnen, M., Korving, J., Brouwer, A., Meijlink, F., and Deschamps, J. (1999). Targeted inactivation of Hoxb8 affects survival of a spinal ganglion and causes aberrant limb reflexes. Mechanisms of Development 89, 103-114.
46. Wolff, M., Alsobrook, J. P., and Pauls, D. L. (2000). Genetic aspects of obsessive-compulsive disorder, Psychiatr Clin North Am 23, 535-44.
47. Yan, Y. L., Joweft, T., and Postlethwait, J. H. (1998). Ectopic expression of hoxb2 after retinoic acid treatment or mRNA injection: disruption of hindbrain and craniofacial morphogenesis in zebrafish embryos, Dev Dyn 213, 370-85.
48. Zwartkruis, F., Hoeijmakers, T., Deschamps, J., and Meijnlinc, F. (1992). The murine Hox-2.4 promoter contains a fumctional octamer motif, Nucleic Acids Res 20, 1599-606.

What is claimed is:

1. A method of screening for an agent or combination of agents that reduces one or more repetitive behaviors, comprising
   A. administering the agent or combination of agents to be screened to a mouse with a HOXB8 gene mutation, wherein the gene mutation is a frameshift mutation resulting in a premature stop codon within the first exon, or is an insertion of a floxed pMC-1neo$^r$ cassette into a homeodomain, and
   B. determining whether one or more repetitive behaviors of the mouse is reduced, the reduction in one or more repetitive behaviors indicating an agent or combination of agents that reduces repetitive behaviors.

2. The method of claim 1, wherein the gene mutation results in reduced expression of gene transcripts.

3. The method of claim 1, wherein the administering step is in vivo.

4. The method of claim 3, wherein the administering step is achieved by intravenous injection of the agent or combination of agents.

5. The method of claim 3, wherein the administering step is achieved by intraventricular injection of the agent or combination of agents.

6. The method of claim 3, wherein the administering step is achieved by intracerebral injection of the agent or combination of agents.

7. The method of claim 3, wherein the administering step is achieved by subdural injection of the agent or combination of agents.

8. The method of claim 3, wherein the administering step is achieved by intrathecal injection of the agent or combination of agents.

9. The method of claim 1, wherein the reduction in one or more repetitive behaviors comprises a reduction in excessive grooming behavior.

10. The method of claim 9, wherein the reduction in excessive grooming behavior comprises a reduction in the total amount of time the mouse grooms.

11. The method of claim 9, wherein the reduction in excessive grooming behavior comprises a reduction in the total number of times the mouse initiates grooming.

12. The method of claim 9, wherein the reduction in excessive grooming behavior comprises a reduction in hair removal caused by grooming.

13. The method of claim 9, wherein the reduction in excessive grooming behavior comprises a reduction in lesions caused by grooming.

14. The method of claim 9, wherein the reduction in excessive grooming behavior comprises a reduction in self-grooming.

15. The method of claim 9, wherein the reduction in excessive grooming behavior comprises a reduction in grooming of other animals.

16. The method of claim 9, wherein the excessive grooming behavior is non-induced or induced.

* * * * *